United States Patent [19]

Davies et al.

[11] Patent Number: 4,838,998
[45] Date of Patent: Jun. 13, 1989

[54] PROCESS FOR SEPARATING SULFURIC ACID AND CARBOXYLIC ACIDS

[75] Inventors: Philip D. T. Davies, Seabrook, Tex.; Lawrence S. Kirch, Meadowbrook, Pa.

[73] Assignee: Rohm and Haas Company, Philadelphia, Pa.

[21] Appl. No.: 128,749

[22] Filed: Dec. 4, 1987

Related U.S. Application Data

[63] Continuation-in-part of Ser. No. 809,323, Dec. 19, 1985, abandoned, which is a continuation-in-part of Ser. No. 690,076, Jan. 9, 1985, abandoned.

[51] Int. Cl.$^4$ ............................................. B01D 3/34
[52] U.S. Cl. .................................... 203/96; 203/15; 203/92; 203/DIG. 8; 562/521; 260/419; 159/DIG. 8
[58] Field of Search ............ 203/15, 91, 92, 95, 203/96, 25, DIG. 8; 202/205; 260/423, 419; 562/521; 159/DIG. 8, DIG. 16

[56] References Cited

U.S. PATENT DOCUMENTS

| | | | |
|---|---|---|---|
| 2,831,877 | 4/1958 | Koch | 260/413 |
| 2,876,241 | 3/1959 | Koch et al. | 562/521 |
| 3,262,954 | 7/1966 | Wehe, Jr. et al. | 562/521 |
| 3,282,973 | 11/1966 | Devine et al. | 260/413 |
| 3,296,286 | 1/1967 | Wehe Jr. et al. | 562/521 |
| 3,600,283 | 8/1971 | Bollen et al. | 427/352 |
| 3,632,638 | 1/1972 | Hyman | 562/521 |
| 3,663,613 | 5/1972 | Pai et al. | 562/521 |
| 3,665,034 | 5/1972 | Komatsu et al. | 562/521 |
| 3,775,449 | 11/1973 | Yeomans | 562/521 |
| 3,838,018 | 9/1974 | Gehrmann et al. | 203/96 |
| 4,358,609 | 11/1982 | Hardy | 562/606 |
| 4,452,999 | 6/1984 | Besecke et al. | 562/521 |
| 4,504,675 | 3/1985 | Besecke et al. | 562/521 |

FOREIGN PATENT DOCUMENTS

| | | | |
|---|---|---|---|
| 7318216 | 5/1969 | Japan | 562/521 |
| 0743597 | 1/1956 | United Kingdom | 562/521 |

Primary Examiner—Kenneth M. Schor
Assistant Examiner—V. Manoharan
Attorney, Agent, or Firm—Terence P. Strobaugh

[57] ABSTRACT

The amount of water required to effect efficient separation of a mixture of sulfuric acid and carboxylic acids by distillation, is reduced, by diluting the mixture while in the distillation column in a prescribed manner with sufficient water to provide a water:sulfuric acid mole ratio of about 1:1. The heat generated by the internal dilution reduces the energy requirement of the column. Feeding the dilution water to the column below the feed mixture is a key element of the process.

5 Claims, No Drawings

PROCESS FOR SEPARATING SULFURIC ACID AND CARBOXYLIC ACIDS

BACKGROUND OF THE INVENTION

This is a continuation-in-part of Ser. No. 809,323, filed Dec. 19, 1985, now abandoned, which is a continuation-in-part of Ser. No. 690,076 filed Jan. 9, 1985 now abandoned.

This invention relates to the separation of a mixture of sulfuric acid and a carboxylic acid such as that produced from a sulfuric acid-catalyzed carbonylation of olefinic compounds.

In commercial processes it is important to obtain a clean separation of the components of a product mixture for efficient recycle of one or more of the components and for recovery of useful products in high yields. In addition, careful attention must be given to costs of energy, such as may be required in distillation or other separation techniques, in order to make the overall process economical and competitive.

Illustrative of a process to which the foregoing considerations are applicable is the separation of sulfuric acid (for recycle) and a alkanoic acid (as product) from the reaction product mixture of a sulfuric acid catalyzed carbonylation of olefins (Koch process—U.S. Pat. No. 2,831,877). The carboxylic acids resulting from the process can be used for a wide variety of purposes but are particularly suited as the feed in large scale oxydehydrogenation processes for the production of unsaturated carboxylic acids.

Sulfuric acid and carboxylic acid have been separated by vacuum evaporation such as described in U.S. Pat. Nos. 3,632,638 (Hyman) and 3,663,613 (Pai and Hyman). In this method the addition of a large amount of water to the feed mixture in the evaporation apparatus is known to promote the separation of the acids.

A combination of solvent extraction and distillation provides good separation of the components of a sulfuric acid/carboxylic acid mixture but again a large amount of dilution water is required which must be boiled off overhead, and the solvent must be removed.

OBJECTS AND SUMMARY

Accordingly, an object of the invention is to provide a more effective, less energy intensive and therefore more economical method for separating sulfuric acid and carboxylic acid, such as may be produced by the sulfuric acid catalyzed carbonylation of olefins to carboxylic acids according to the Koch synthesis.

A prime object is to minimize the amount of water which is required to be added to a mixture of sulfuric acid and carboxylic acid when separating such components from, for example, the reaction product mixture from the Koch synthesis, with consequent savings in the cost of removing the water from the recovered sulfuric acid prior to its recycle to the carbonylation reactor.

These and other objectives, features and advantages of the invention are achieved by feeding a sulfuric acid/carboxylic acid mixture to a distillation column, diluting the mixture while in the column in a prescribed manner with sufficient water to provide a distillation mixture having a water:sulfuric acid mole ratio of about 1:1, and distilling the mixture.

For purposes of further discussion the foregoing dilution technique is hereinafter sometimes described as "internal dilution" as contrasted with the "external dilution" of prior practice as described in the Hyman and Pai/Hyman patents identified above. However, it should be recognized that while internal dilution of the column feed is a necessary part of the invention, internal dilution alone will not facilitate high recoveries of the carboxylic acid at net water:sulfuric acid mole ratios less than about 2:1. The method of effecting the internal dilution is a key element of the invention.

U.S Pat. No. 3,663,613 (Pai) neither specifically mentions nor give any examples of multistage distillations. Multistage distillation as applied to the separation under discussion is simply cofeeding the sulfuric acid/carboxylic acid/water mixture and the dilution water usually to the top tray of a multistage column and will not result in high recoveries of the carboxylic acid unless the net water:sulfuric acid mole ratio exceeds 2.0.

At mole ratios less than 2.0, if one analysed the composition of the liquid on each tray below the feed tray and determined concentration profiles for each component in the column, he would find that the water concentration was highest at the top of the column and the sulfuric acid concentration was highest at the bottom of the column. Moreover, there would be very little overlap of the water and sulfuric acid profiles and it is because of this that significant levels of the carboxylic acid would be found in the bottoms stream leaving the column. Sulfuric acid will only relinquish its hold on the carboxylic acid if a significant water concentration in the strong acid is maintained. The carboxylic acid yield loss would be compounded in the sulfuric acid reconcentration column where the high bottoms temperatures that must be employed there would result in the degradation of the residual organic values producing a black recycle acid with a high tar content.

Only when the dilution water is fed separately towards the bottom of the column, can one modify the concentration profiles in the column so that water and sulfuric acid coexist in substantial quantities over a large portion of the column. It is the overlapping of the water and sulfuric acid concentration profiles that facilitates the high recovery of the carboxylic acid at water:sulfuric acid mole ratios approaching 1.0. As a bonus, since the sulfuric acid leaving the bottom of the column is substantially free of the carboxylic acid, the recycle sulfuric acid produced in the subsequent reconcentration column is substantially free of tar.

Among the advantages achieved by the internal dilution is the use of the large amount of energy released during the internal dilution to raise the temperature within the column. Consequently, the distillation does not depend solely on an external heat source. The location of the water addition (below the carbonylation mixture feed point) in the bottom of the column which permits substantially complete separation of the sulfuric and carboxylic acids using a minimum amount of water, in many cases enabling effective separation at a water:sulfuric acid mole ratio of only about 1:1. In large scale processes this translates into very substantial energy savings due to the lower amounts of water which must be boiled off for recovery of concentrated sulfuric acid in a downstream distillation column.

For example, the dilution of a mixture of 85 weight percent sulfuric acid and 15 percent isobutyric acid with sufficient water to yield a solution that is 72.7% sulfuric acid, 12.8% isobutyric acid, and 14.5% water (water:sulfuric acid mole ratio equal to 1.09) requires 1.13 pounds of water per pound of isobutyric acid. If this dilution and the subsequent distillation is performed according to the teachings of this invention, the distillate from the column will have a composition of about 91% isobutryric acid/9% water and contain virtually all of the isobutyric acid in the column feed. The bottoms stream from the column will have a composition of about 86% sulfuric acid/14% water. The bottoms stream can then be reconcentrated (for recycle) to 96% sulfuric acid.

The net amount of water distilled overhead in both columns taken together will be about 0.89 pounds per pound of isobutyric acid recovered. If the separation were to be repeated using the prior art and a 2.0 molar ratio of water:sulfuric acid, 1.85 pounds of water would have to be taken overhead per pound of isobutyric acid recovered. The net difference between the two cases is 0.96 pounds of water per pound of isobutyric acid. The incremental energy cost required to distill this additional water would be substantial for a world-scale isobutyric acid plant.

DETAILED DESCRIPTION

The separation method of the invention is practiced on a mixture of sulfuric acid, a carboxylic acid and water. A preferred industrial application is the separation of the components of an effluent product stream from the sulfuric acid catalyzed carbonylation of an olefin. The sulfuric acid for the carbonylation is concentrated, i.e., at least 90%, preferably at least 96%. The product stream from the carbonylation generally will contain from about 50 to about 90 weight percent of sulfuric acid (100% basis), from about 10 to about 50 weight percent of carboxylic acid or water azeotrope thereof, and up to about 5 weight percent of water. Mixtures outside these ranges may be separated but as a practical matter the proportions are limited by the solubilities of the components to the stated ranges. By careful carboxylation, the water may be eliminated or reduced to less than 5 weight percent, and the carbonylation product streams used as feed in the separation process of the invention will contain about 75-85 weight percent sulfuric acid, about 15-25 weight percent carboxylic acid, and up to about 4 weight percent water.

The carboxylic acids may contain from 2 to about 30 carbon atoms depending upon the olefins from which they are derived. The lighter carboxylic acids, i.e. those having about 8 to 10 carbon atoms generally have pure component boiling points lower than that of concentrated sulfuric acid.

In those cases where high boiling carboxylic acids are to be recovered as their respective water azeotropes, additional dilution water will be required in an amount dictated by the composition of the stream taken overhead in the distillation apparatus.

Note, however, that in cases where azeotropes are described in the literature for carboxylic acid-water binary systems, the overhead stream from the distillation apparatus that derives from the ternary system (i.e. carboxylic acid-water-sulfuric acid) may be richer in the in the ternary system (i.e. carboxylic acid-water-sulfuric acid may be richer in the carboxylic acid) than the binary data might suggest. This is true, for example, for mixtures containing isobutyric acid.

Many of the carboxylic acids, including the heavier ones, form azeotropes with water and boil at correspondingly lower temperatures.

Typical of the olefinic precursor compounds are aliphatic olefins, such as ethylene, propylene, butylene, and isobutylene, or higher molecular weight olefins such as nonene, hexadecene, and the like, including mixtures thereof; cyclic olefins such as cyclehexene; aliphatic or alicyclic diolefins such as butadiene and 4-vinylcyclohexene-1; other polyolefinic compounds which lead to unsaturated carboxylic acids such as oleic acid; and olefinic compounds containing other functional groups, such as 1,2-dichloroethylene and cinnamyl alcohol.

The corresponding carboxylic acids include propionic acid, isobutyric acid, trimethylacetic acid, and the like, such as are disclosed in U.S. Pat. Nos. 2,831,877 and 3,282,973. Other carboxylic acids, not synthesized directly by the Koch process, are also separable from sulfuric acid by the process of the invention. These include phthalic acid, acrylic acid, methacrylic acid, and the like. The invention is also applicable to mixtures of carboxylic acids.

The mixture of sulfuric acid, carboxylic acid and water (if any) is distilled in a conventional distillation column equipped with a reboiler, bottoms product receiver, overhead condenser, overhead receiver and other known controls and elements.

Although for some carboxylic/sulfuric mixtures it is possible to distill at atmospheric pressure it is generally preferrable to operate under vacuum distillation conditions, for example, at about 25-100 mm Hg pressure, preferably about 30-50 mm, and more preferably, 35-45 mm.

The distillation bottoms temperature should avoid regions where the carboxylic acid decomposes. At a distillation pressure of 35 mm for the distillation of a sulfuric acid/isobutyric acid mixture, this temperature will be in the range of from 100°-160° C. for continuous distillations and not over about 120° C. for batch distillations. These conditions will vary, of course, with the carboxylic acid to be separated from the sulfuric acid.

Continuous, thin film vacuum distillation or distillation in packed or tray columns can be suitable distillation techniques. However, the latter distillation method is preferable since thin film columns generally have very few theoretical contact stages and thus compromise one of the key requirements of the instant invention, i.e. multiple stages.

In the preferred operation of the separation process, the dilution water is fed to the column at a point below the sulfuric acid/carboxylic acid feed. This promotes greater interaction between the sulfuric acid and the water by preventing the water from "flashing" through the sulfuric acid. For example, in a 20-tray Oldershaw column, if the sulfuric acid/carboxylic acid mixture is fed at tray 17 (counting from the bottom of the column), the dilution water is preferably fed at about tray 10 or lower. (A reflux stream is generally not required and the few trays above the feed tray then act only as entrainment separators.

The amount of dilution water should be such as to provide (at least) about a 1:1 mole ratio of water to sulfuric acid. The amount of dilution water must be such as to maintain the water/sulfuric acid mole ratio as close to 1:1 as possible, for example in the range of 1:1 to 1.5:1, in order to minimize the amount of water which must be removed from the sulfuric acid prior to its reuse.

It is preferred that the dilution water be sufficient to provide from about 65 to about 75 weight percent sulfuric acid, from about 15 to about 25 weight percent isobutyric acid and from about 12 to about 15 weight percent total water in the distillation mixture at the outset of the distillation. Illustratively, for the separation of a feed mixture containing about 85 weight percent sulfuric acid and about 15 weight percent isobutyric acid, internal dilution of the mixture to 73.5 weight percent sulfuric acid, 13.0 weight percent isobutyric acid and 13.5 weight percent water provides a water:sulfuric acid mole ratio of 1:1, the optimum mole ratio for best separation. Isobutyric acid recovery under the preferred conditions of the separation process will be 97% or higher. The process generally will provide a bottoms stream containing 80-90% sulfuric acid which can be further concentrated by subsequent distillation, if desired.

Other conditions and aspects of the separation method are conventional and will be readily apparent to those skilled in the art. For example, it may be advantageous to utilize inert gas (e.g., nitrogen) stripping in conjunction with the distillation, or to recycle product to the same or another distillation apparatus for additional separation.

The following further illustrates the invention but is not intended to be all inclusive or is necessarily limits the scope of the invention. All parts and percentages are by weight unless otherwise stated.

EXAMPLES

Run Nos. 1 and 2

Internal Dilution

From the carbonylation of propylene with concentrated sulfuric acid and carbon monoxide at a pressure above 100 atmospheres, there was obtained a product mixture containing 15% by weight isobutyric acid (IBA, selectivity 95%) and 85% by weight sulfuric acid. This reactor effluent was fed to a distillation apparatus consisting of a stirred bottoms vessel with overflow level control, a 20-plate Oldershaw column (tray 20 is at top of column), and a water cooled condenser. The carbonylation effluent was fed to tray 12 of the Oldershaw column. Enough water to achieve a 1.26:1 molar ratio with the sulfuric acid was fed to tray 10 of the column. The bottoms pot was maintained at 150°-160° C. and the residence time of the material therein was about 25 minutes. The distillation was effected at an overhead pressure of 35 mm Hg and resulted in the recovery of 99% of the IBA overhead and a bottoms product consisting of 82% sulfuric acid. Further concentration of the sulfuric acid by distillation produced a catalyst suitable for recycle to the carbonylation process. The conditions and results of this experiment are summarized as Run 2 of Table I below.

External Dilution

By way of contrast, when the carbonylation product effluent was diluted prior to being fed to the distillation column, the bottoms stream contained 1.7% by weight IBA and charred considerably to give a pitch black color when concentrated. In this distillation the material boiled at 90° C. (35 mm Hg). This result is summarized as Run 1 of Table I below.

Table I summarizes the results of the foregoing Runs and other runs wherein it is shown that feeding the carbonylation product to the column at a still higher level, i.e., at tray 17 rather than tray 12 as in Runs 4, 7 and 9, provided additional improvement. This improvement is particularly evident when comparing Runs 3 and 4. Run 3, although operated at close to a 1:1 mole ratio of water to sulfuric acid resulted in 3.4% IBA in the bottoms stream and thus the separation is labelled "unacceptable" ("acceptable" means about 97-99% IBA recovery; "unacceptable" is less than 97% IBA recovery). The IBA recovery was improved by the greater spacing of the feed and water addition trays in Run 4. Runs 5, 6, 8 and 10 describe distillations wherein the water:sulfuric acid mole ratios were less than 1:1 and therefore provided poorer ("unacceptable") separations. Runs 2, 4, 7 and 9 are representative of the process of the invention; the remaining runs show other, disadvantageous separation conditions.

TABLE I

| Run No. | Carbonylation Product Feed | | Overall Dilution | | | Internal Dilution | Mole Ratio $H_2SO_4:H_2O$ | Carbonylation Product Feed Tray | Water Feed Tray | Separation |
|---|---|---|---|---|---|---|---|---|---|---|
| | $H_2SO_4$ % | IBA % | $H_2SO_4$ % | IBA % | Water % | | | | | |
| 1. | 82.5 | 17.5 | 69.8 | 14.9 | 15.3 | No | 1:1.19 | 12 | — | Unacceptable |
| 2. | 85 | 15 | 71.0 | 12.5 | 16.5 | Yes | 1:1.26 | 12 | 10 | Acceptable |
| 3. | 85 | 15 | 72.9 | 12.8 | 14.3 | Yes | 1:1.07 | 12 | 10 | Unacceptable |
| 4. | 85 | 15 | 72.7 | 12.8 | 14.5 | Yes | 1:1.09 | 17 | 10 | Acceptable |
| 5. | 85 | 15 | 75.5 | 13.2 | 11.8 | Yes | 1:0.86 | 17 | 10 | Unacceptable |
| 6. | 85 | 15 | 75.0 | 13.2 | 11.8 | Yes | 1:0.86 | 17 | 4 | Unacceptable |
| 7. | 80 | 20 | 68.8 | 17.2 | 14.0 | Yes | 1:1.11 | 17 | 10 | Acceptable |
| 8. | 80 | 20 | 70.7 | 17.7 | 11.6 | Yes | 1:0.89 | 17 | 10 | Unacceptable |
| 9. | 75 | 25 | 64.9 | 21.6 | 13.5 | Yes | 1:1.13 | 17 | 10 | Acceptable |
| 10. | 75 | 25 | 67.0 | 22.3 | 10.7 | Yes | 1:0.87 | 17 | 10 | Unacceptable |

What is claimed is:

1. A method of separating components of a mixture comprising from about 10 to about 50 weight percent of a isobutyric acid having, by itself or as an azeotrope with water, a boiling point lower than that of sulfuric acid, from about 75 to 85 weight percent of sulfuric acid, and up to about 5 weight percent of water, which comprises feeding the mixture into a multistage distillation column operated at a temperature in the range of from about 100° C. to about 160° C. and at a pressure of from about 30 mm to about 50 mm; feeding dilution water into the column below the point of entry of said mixture; diluting the mixture while in the column with said dilution water to provide a distillation mixture having a water:sulfuric acid mole ratio of from 1:1 to 1.5:1; and distilling the mixture, wherein the dilution water is fed into the column at an amount sufficient to provide from about 10 to about 20 weight percent total water in the distillation mixture at the outset of the distillation;

2. The method of claim 1 wherein the distillation is a continuous distillation of the feed mixture and the amount of dilution water is sufficient to provide a water:sulfuric acid mole ratio of about 1:1 in the distillation mixture at the outset of the distillation.

3. The method of claim 1 wherein the dilution water is sufficient to provide from about 65 to about 75 weight percent sulfuric acid, from about 15 to about 25 weight percent isobutyric acid and from about 12 to about 15 weight percent total water in the distillation mixture at the outset of the distillation.

4. The method in claim 1 wherein the mixture is an effluent stream from the sulfuric acid catalyzed carbonylation of an olefinic compound.

5. The method of claim 4 wherein the mixture is an effluent stream from the sulfuric acid catalyzed carbonylation of propylene.

* * * * *